(12) United States Patent
Fukumatsu et al.

(10) Patent No.: US 8,847,367 B2
(45) Date of Patent: Sep. 30, 2014

(54) ORGANIC ELECTROLUMINESCENT DEVICE

(75) Inventors: Takayuki Fukumatsu, Kitakyushu (JP); Ikumi Ichihashi, Kitakyushu (JP); Hiroshi Miyazaki, Kitakyushu (JP); Atsushi Oda, Yamagata (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 1038 days.

(21) Appl. No.: 12/922,635

(22) PCT Filed: Feb. 27, 2009

(86) PCT No.: PCT/JP2009/053716
§ 371 (c)(1),
(2), (4) Date: Nov. 12, 2010

(87) PCT Pub. No.: WO2009/119249
PCT Pub. Date: Oct. 1, 2009

(65) Prior Publication Data
US 2011/0101319 A1    May 5, 2011

(30) Foreign Application Priority Data
Mar. 27, 2008 (JP) ................................ 2008-083672

(51) Int. Cl.
| | | |
|---|---|---|
| *H01L 23/58* | (2006.01) | |
| *C07D 493/14* | (2006.01) | |
| *H01L 51/00* | (2006.01) | |
| *C07D 487/04* | (2006.01) | |
| *H01L 51/50* | (2006.01) | |

(52) U.S. Cl.
CPC .......... *H01L 51/5088* (2013.01); *C07D 493/14* (2013.01); *H01L 51/005* (2013.01); *C07D 487/04* (2013.01); *H01L 51/0053* (2013.01); *H01L 51/5048* (2013.01); *H01L 2251/552* (2013.01)

USPC .......... 257/643; 257/649; 257/759; 257/769; 257/E21.006; 257/E21.007; 257/E21.053; 257/E21.085; 257/E21.267; 257/E21.32; 257/E21.352

(58) Field of Classification Search
USPC ......... 257/643, 649, 759, 769, 918, 602, 603, 257/40, 78, 79, 88, 152, 431, E21.006, 257/E21.007, E21.053, E21.085, E21.267, 257/E21.32, E21.352
See application file for complete search history.

(56) References Cited

U.S. PATENT DOCUMENTS

| | | | |
|---|---|---|---|
| 4,720,432 A | | 1/1988 | VanSlyke et al. |
| 6,558,819 B1 * | | 5/2003 | Igarashi ........................ 428/690 |
| 6,670,645 B2 * | | 12/2003 | Grushin et al. ................. 257/98 |
| 7,318,966 B2 * | | 1/2008 | Tominaga et al. ............. 428/690 |
| 7,604,874 B2 * | | 10/2009 | Kim et al. ...................... 428/690 |
| 7,901,794 B2 * | | 3/2011 | Sugimoto et al. ............. 428/690 |
| 8,076,839 B2 * | | 12/2011 | Kuma et al. ................... 313/504 |
| 8,106,391 B2 * | | 1/2012 | Endo et al. ...................... 257/40 |
| 8,269,215 B2 * | | 9/2012 | Katz et al. ....................... 257/40 |
| 2007/0160905 A1 | | 7/2007 | Morishita et al. |

FOREIGN PATENT DOCUMENTS

| | | |
|---|---|---|
| JP | 63-295695 A | 12/1988 |
| JP | 4-320486 A | 11/1992 |
| JP | 11-35687 A | 2/1999 |
| JP | 2004-143044 A | 5/2004 |
| JP | 2008-198769 A | 8/2008 |
| WO | WO 2005/109542 A1 | 11/2005 |
| WO | WO 2007/080801 A1 | 7/2007 |

OTHER PUBLICATIONS

English translation of the International Preliminary Report on Patentability issued Nov. 9, 2010, in PCT International Application No. PCT/JP2009/053716.
English translation of the Written Opinion of the International Searching Authority issued Nov. 4, 2010, in PCT International Application No. PCT/JP2009/053716.
Notification Concerning Transmittal of International Preliminary Report on Patentability mailed Oct. 7, 2010, in PCT International Application No. PCT/JP2009/053716.
International Search Report dated Mar. 31, 2009 in International Application No. PCT/JP2009/053716.

International Preliminary Report on Patentability issued Oct. 7, 2010, in corresponding PCT International Application No. PCT/JP2009/053716.
Notification of Concerning Transmittal of International Preliminary Report on Patentability issued Oct. 7, 2010, in corresponding PCT International Application No. PCT/JP2009/053716.

* cited by examiner

*Primary Examiner* — David Nhu
(74) *Attorney, Agent, or Firm* — Birch, Stewart, Kolasch & Birch, LLP

(57) ABSTRACT

Provided are a hole-injecting material for an organic electroluminescent device (organic EL device) exhibiting high luminous efficiency at a low voltage and having greatly improved driving stability, and an organic EL device using the material. The hole-injecting material for an organic EL device is selected from benzenehexacarboxylic acid anhydrides, benzenehexacarboxylic acid imides, or N-substituted benzenehexacarboxylic acid imides. Further, the organic EL device has at least one light-emitting layer and at least one hole-injecting layer between an anode and a cathode arranged opposite to each other, and includes the above-mentioned hole-injecting material for an organic EL device in the hole-injecting layer. The organic EL device may contain a hole-transporting material having an ionization potential (IP) of 6.0 eV or less in the hole-injecting layer or a layer adjacent to the hole-injecting layer.

4 Claims, 3 Drawing Sheets

ORGANIC ELECTROLUMINESCENT DEVICE

TECHNICAL FIELD

The present invention relates to an organic electroluminescent device (hereinafter, sometimes abbreviated as an organic EL device or a device) utilized in a planar light source and a display device.

BACKGROUND ART

The development of an organic EL device is being actively pursued from the viewpoints of the applications to displays and lighting. The driving principle of the organic EL device is as described below. That is, holes and electrons are injected from an anode and a cathode, respectively. The holes and electrons are transported through an organic thin film and recombine with each other in a light-emitting layer to form an excited state. Then, the excited state emits light. In order to increase luminous efficiency, the holes and electrons must be efficiently injected and transported through the organic thin film. However, the transfer of carriers in the organic EL device is restricted by an energy barrier between an electrode and an organic thin film and a low carrier mobility in the organic thin film. Thus, there is a limitation on an improvement in luminous efficiency.

Methods which have been devised to solve such problem include a method involving improving hole-injecting property from an anode and transporting holes to a light-emitting layer at a lower voltage by the insertion of a hole-injecting layer between an anode and a hole-transporting layer.

For example, Patent Document 1 discloses that the use of a phthalocyanine-based metal complex in the hole-injecting layer allows for a reduction in driving voltage and an improvement in driving stability of a device. However, there has been a problem in that luminous efficiency is lowered because the phthalocyanine-based metal complex has absorption in a visible light region. Further, there has also been a problem in that the chromaticity is difficult to be controlled in color development.

Further, Patent Document 2 discloses an organic EL device provided with an n-p junction layer formed of an n-type organic layer adjacent to an anode and a p-type organic layer provided on the n-type organic layer. Further, Patent Document 2 discloses an organic electroluminescent device in which the difference between the LUMO energy level of the n-type organic layer and the Fermi energy level of the anode is 2.0 eV or less, and the difference between the LUMO energy level of the n-type organic layer and the HOMO energy level of the p-type organic layer is 1.0 eV or less. Here, the n-type organic layer can be interpreted as a hole-injecting layer. Further, the p-type organic layer can be interpreted as a hole-transporting layer or a light-emitting layer.

In addition, Patent Document 2 discloses, as an electron donating compound used for the n-type organic layer, 2,3,5,6-tetrafluoro-7,7,8,8-tetracyanoquinodimethane (F4TCNQ), fluorine-substituted 3,4,9,10-perylenetetracarboxylic acid dianhydride (PTCDA), cyano-substituted PTCDA, naphthalenetetracarboxylic acid dianhydride (NTCDA), fluorine-substituted NTCDA, cyano-substituted NTCDA, or hexanitrile hexaazatriphenylene (HAT).
Patent Document 1: JP 63-295695 A
Patent Document 2: WO 2005/109542 A1

DISCLOSURE OF THE INVENTION

Problem to be Solved by the Invention

An object of the present invention is to provide an organic EL device that exhibits high luminous efficiency even at a low voltage, shows little time-dependent change during continuous driving, and has high quality.

Means for Solving the Problem

The present invention relates to a hole-injecting material for an organic electroluminescent device, the material including a carboxylic acid derivative represented by the following general formula (1):

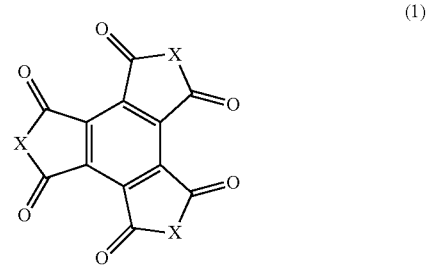

(1)

where: X represents O or N—R; and R represents H or a monovalent substituent.

Further, the present invention relates to an organic electroluminescent device including at least one light-emitting layer and at least one hole-injecting layer between an anode and a cathode arranged opposite to each other, in which the organic electroluminescent device includes a hole-injecting layer containing the carboxylic acid derivative represented by the above-mentioned general formula (1).

In addition, the present invention relates to an organic electroluminescent device including a hole-transporting material having an ionization potential (IP) of 6.0 eV or less in at least one layer of the above-mentioned hole-injecting layer and a layer adjacent to the hole-injecting layer. The above-mentioned layer adjacent to the hole-injecting layer is preferably a hole-transporting layer or a light-emitting layer. Moreover, the hole-transporting material having an IP of 6.0 eV or less is preferably an arylamine-based hole-transporting material.

BEST MODE FOR CARRYING OUT THE INVENTION

Figure 1:
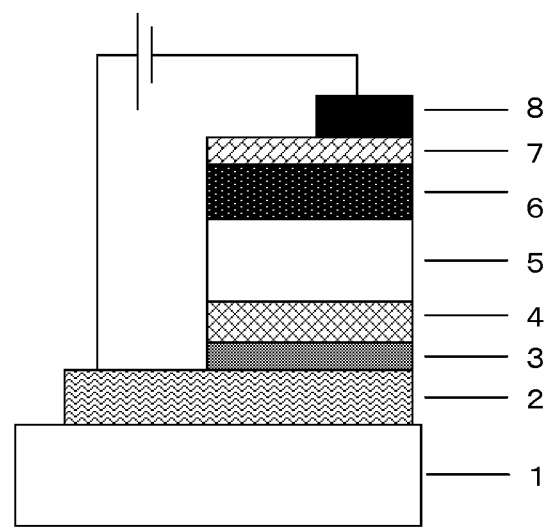
FIG. 1 is a schematic cross-sectional view illustrating an example of an organic EL device of the present invention.

A hole-injecting material for an organic EL device of the present invention is a carboxylic acid derivative represented by the above-mentioned general formula (1).

The organic EL device of the present invention has at least one light-emitting layer and at least one hole-injecting layer between an anode and a cathode arranged opposite to each other, and has a hole-injecting layer containing the carboxylic acid derivative represented by the above-mentioned general formula (1).

First, the carboxylic acid derivative represented by the above-mentioned general formula (1) or the hole-injecting material for an organic EL device is described.

In the general formula (1), X represents O or N—R. Here, R represents hydrogen or a monovalent substituent that is bonded to a nitrogen atom. Preferred examples of the substituent are given below.

That is, there are exemplified: an alkyl group having 1 to 20 or preferably 1 to 6 carbon atoms (such as a methyl group, an ethyl group, a propyl group, an isopropyl group, a tert-butyl group, a pentyl group, a hexyl group, an octyl group, a dodecyl group, a tridecyl group, a tetradecyl group, or a pentadecyl group); a cycloalkyl group having 3 to 20 or preferably 5 to 10 carbon atoms (such as a cyclopentyl group or a cyclohexyl group); an alkenyl group having 2 to 20 or preferably 2 to 6 carbon atoms (such as a vinyl group or an allyl group); an alkynyl group having 2 to 20 or preferably 2 to 6 carbon atoms (such as an ethynyl group or a propargyl group); an aryl group having 6 to 20 or preferably 6 to 10 carbon atoms (such as a phenyl group or a naphthyl group); an aromatic heterocyclic group having 3 to 20 or preferably 5 to 10 carbon atoms (such as a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, or a phthalazinyl group); a heterocyclic group having 3 to 20 or preferably 5 to 10 carbon atoms (such as a pyrrolidyl group, an imidazolidyl group, a morpholyl group, or an oxazolidyl group); a fluorohydrocarbon group having 1 to 20 or preferably 1 to 6 carbon atoms (such as a fluoromethyl group, a trifluoromethyl group, a pentafluoroethyl group, or a pentafluorophenyl group); a cyano group; a nitro group; and a silyl group (such as a trimethylsilyl group, a triisopropylsilyl group, a triphenylsilyl group, or a phenyldimethylsilyl group).

Each of those substituents may be further substituted by the above-mentioned substituent, a halogen, or the like. For example, the aryl group, the aromatic heterocyclic group, or the heterocyclic group may be further substituted by an alkyl group, a halogen, or the like. When each of the substituents is further substituted, the number of carbon atoms to be calculated includes the number of carbon atoms contained in another substituent by which each of the substituents is substituted. Further, a plurality of those substituents may be bonded to each other to form a ring.

X preferably represents O, NH, or NR where R represents the above-mentioned substituent. X more preferably represents O, NH, or NR where R represents the following substituent. R represents an alkyl group having 1 to 6 carbon atoms, a cycloalkyl group having 5 to 10 carbon atoms, an aryl group having 6 to 10 carbon atoms, an aromatic heterocyclic group having 5 to 10 carbon atoms, a fluorohydrocarbon group having 1 to 6 carbon atoms, or a cyano group. In addition, the cycloalkyl group, the aryl group, or the aromatic heterocyclic group may be substituted by an alkyl group having 1 to 6 carbon atoms or a halogen.

Hereinafter, there are given specific examples of the compound represented by the general formula (1). However, the present invention is not limited thereto.

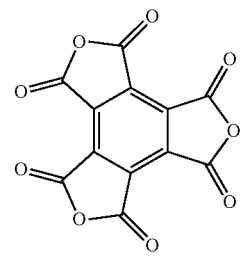

1

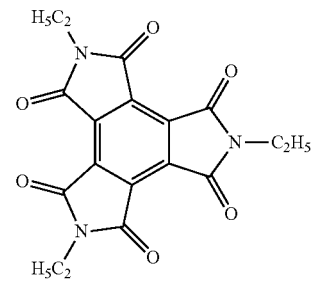

2

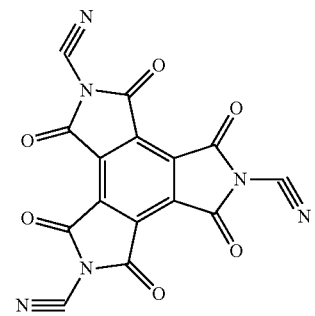

3

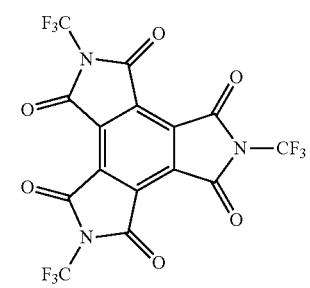

4

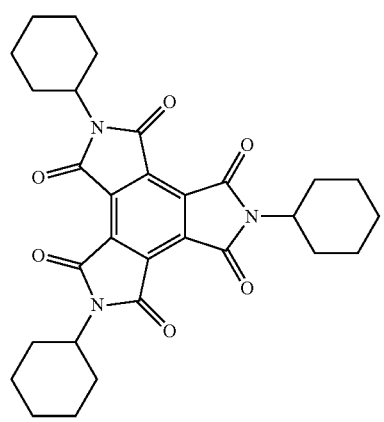

5

5
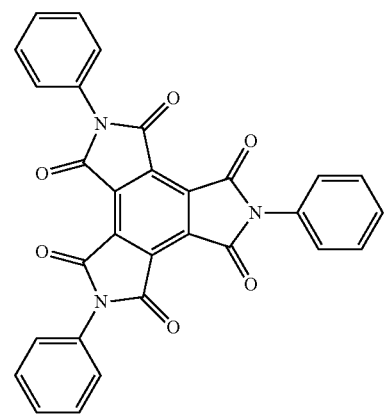
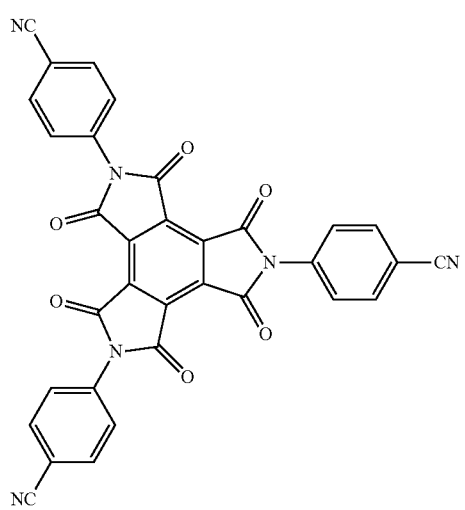
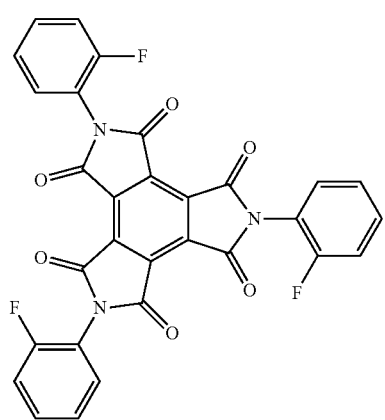
6
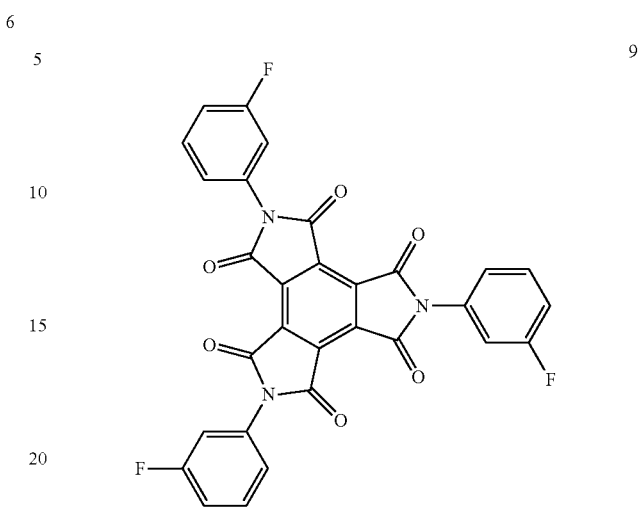
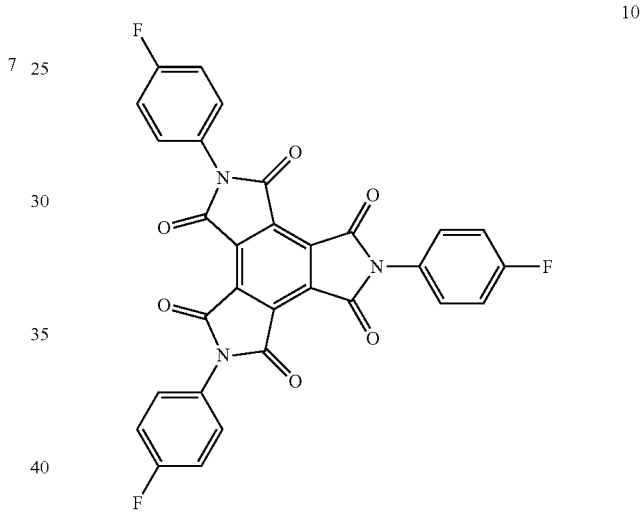
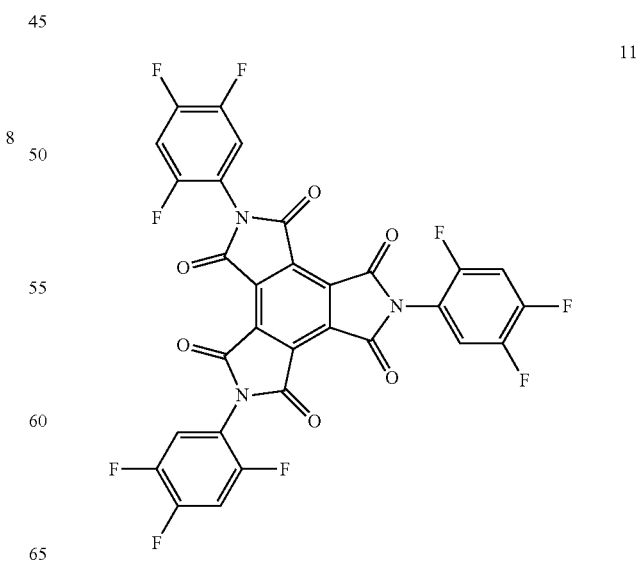

12
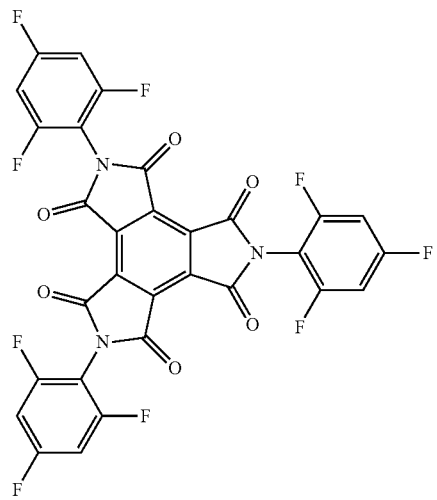
13
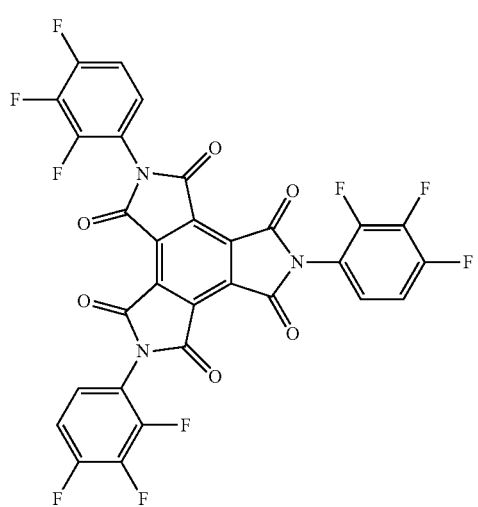
14
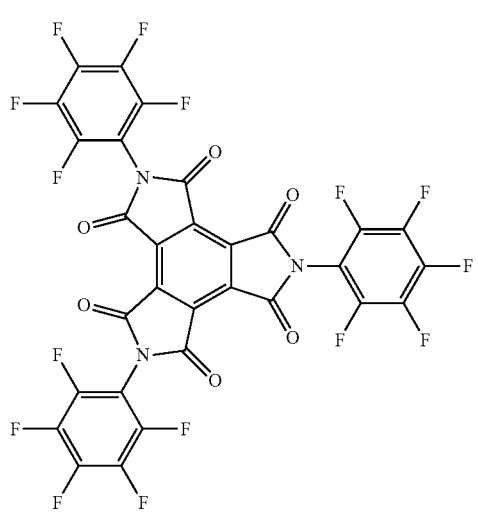
15
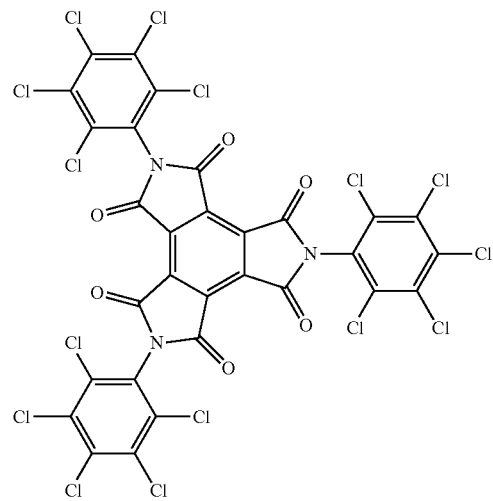
16
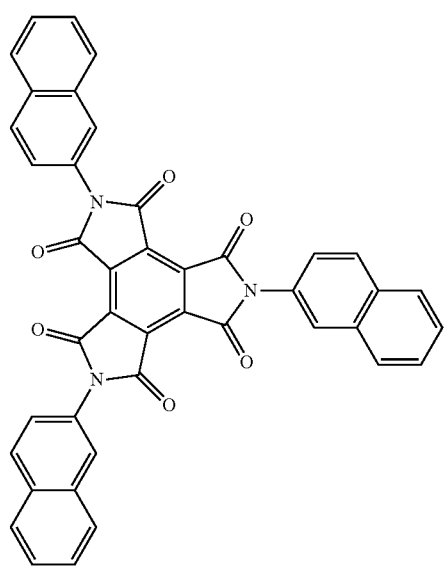
17
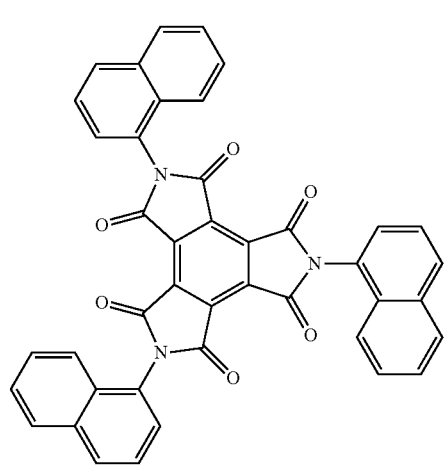

18
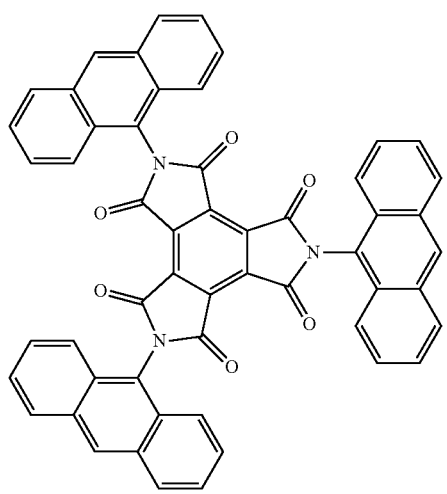
19
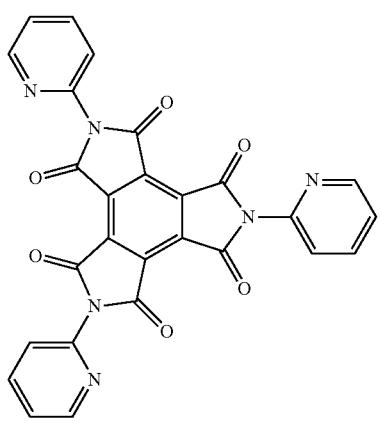
20
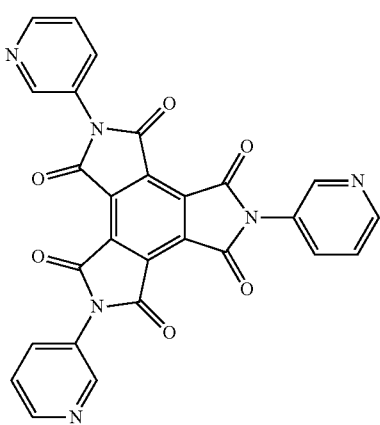
21
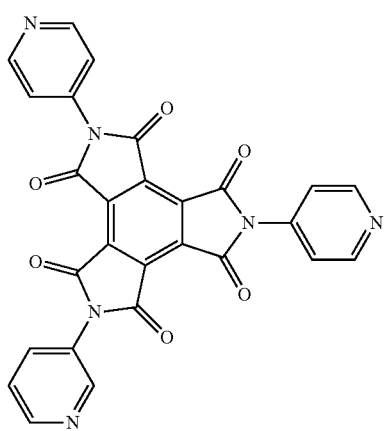
22
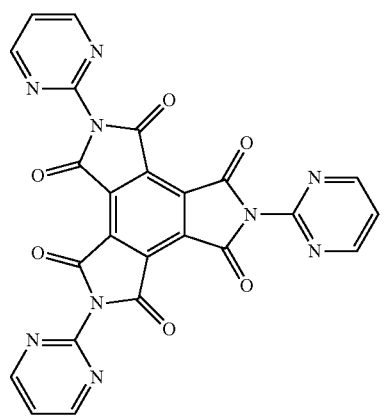
23
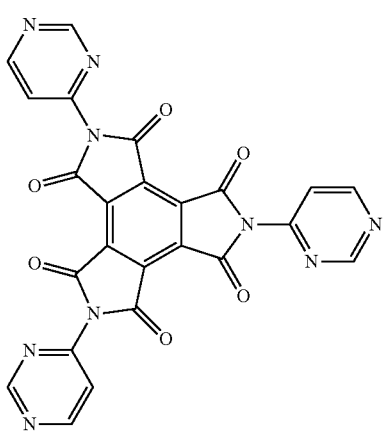

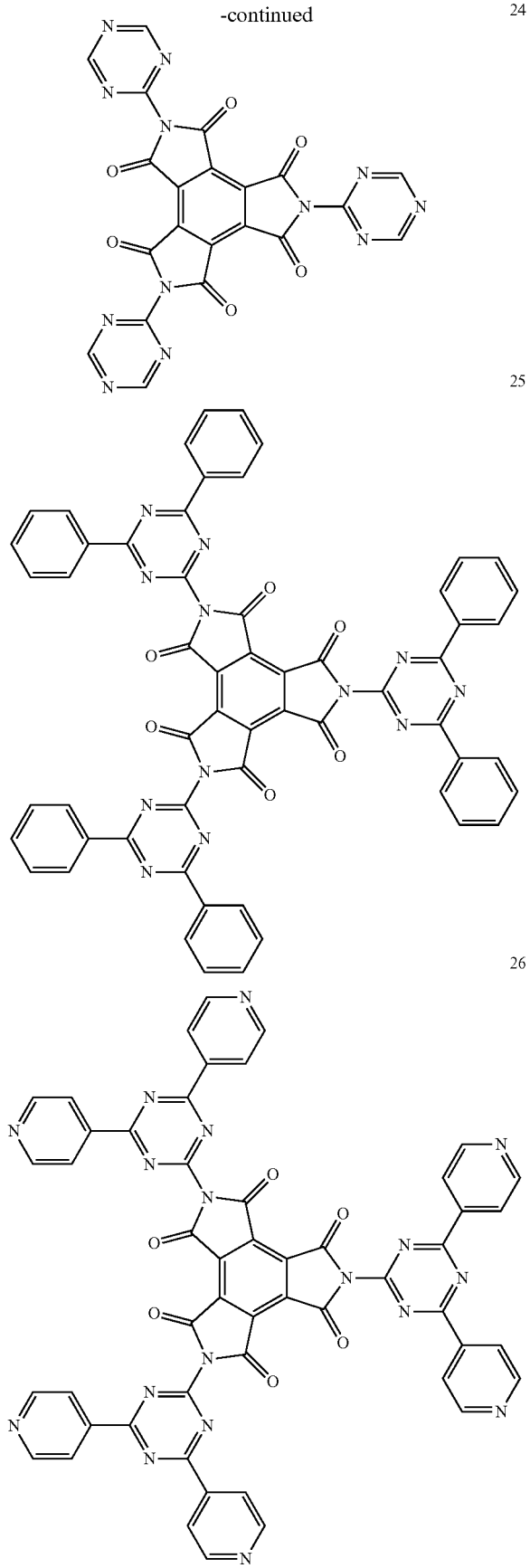

The hole-injecting layer in the organic EL device of the present invention contains a material including at least one kind of compound selected from compounds represented by the above-mentioned general formula (1). The hole-injecting layer may be formed of each of the compounds of the general formula (1) alone or a mixture of the compounds, or may be formed of a mixture with another hole-injecting material. When the compounds are mixed with another hole-injecting material, it is recommended to use the compounds represented by the general formula (1) in an amount of 0.1 wt % or more or advantageously 1 wt % or more. Moreover, it is recommended to use the compounds in an amount of 50 wt % or more or more preferably 80 wt % or more in order to exhibit the effects of the present invention sufficiently.

The hole-injecting layer as used herein refers to a layer provided on the side of an anode with respect to a light-emitting layer, in which the layer contains, as a main active component, a hole-injecting material or a hole-injecting material and a hole-transporting material, and has a function of injecting holes. Thus, the hole-injecting layer may also contain the hole-transporting material in addition to the hole-injecting material. When the hole-injecting layer contains the hole-transporting material, the layer may also be referred to as a hole-injecting/transporting layer, but the layer is appreciated as one aspect of the hole-injecting layer in this description. Further, the hole-injecting material as used herein means a material used for the above-mentioned hole-injecting layer.

When the hole-injecting layer contains the hole-transporting material, the hole-transporting material is preferably a hole-transporting material having an ionization potential (IP) of 6.0 eV or less. A preferred example of the hole-transporting material having an IP of 6.0 eV or less includes an arylamine-based hole-transporting material.

Further, both in the case where the hole-injecting layer contains the hole-transporting material and in the case where the hole-injecting layer does not contain the hole-transporting material, it is preferred that a layer adjacent to the hole-injecting layer contain the hole-transporting material having an IP of 6.0 eV or less. This is more effective in the case where the hole-injecting layer does not contain the hole-transporting material. The layer adjacent to the hole-injecting layer is preferably a hole-transporting layer or a light-emitting layer. In the case of the light-emitting layer, the hole-transporting layer is omitted.

When the hole-injecting layer contains the hole-transporting material, the ratio of the hole-injecting material to the hole-transporting material may vary widely. However, it is recommended that the ratio should fall within the range of 1:9 to 9:1 or preferably 3:7 to 7:3 at a weight ratio. In addition, the hole-injecting layer in this case preferably contains the compound represented by the general formula (1) in an amount of 0.1 wt % or more or advantageously 1 wt % or more. Moreover, it is preferred to use the compound in an amount of 10 wt % or more or more preferably 30 wt % or more in order to exhibit the effects of the present invention sufficiently.

Figure 2:
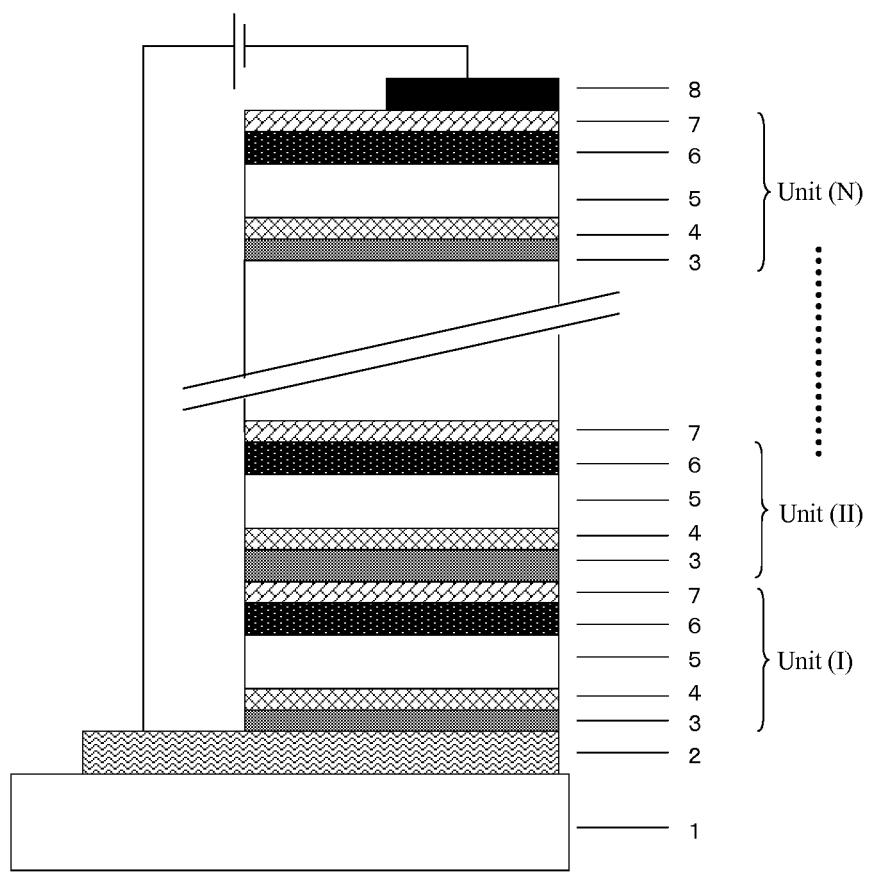
FIG. 2 is a schematic cross-sectional view illustrating an example of a tandem organic EL device.

Hereinafter, the present invention is described with reference to the drawings. FIGS. 1 and 2 are schematic cross-sectional views illustrating examples of the organic EL device of the present invention.

Description of Reference Numerals: 1 substrate; 2 anode; 3 hole-injecting layer; 4 hole-transporting layer; 5 light-emitting layer; 6 electron-transporting layer; 7 electron-injecting layer; and 8 cathode.

First, the configuration of the organic EL device is described.

FIG. 1 illustrates a basic configuration example of the organic EL device of the present invention. The device has a configuration that an anode 2, a hole-injecting layer 3, a hole-transporting layer 4, a light-emitting layer 5, an electron-transporting layer 6, an electron-injecting layer 7, and a cathode 8 are provided on a substrate 1. When the hole-transporting material is contained in at least one layer of the hole-injecting layer and the light-emitting layer, there is no need to provide the hole-transporting layer. When an electron-transporting material is contained in at least one layer of the light-emitting layer and the electron-injecting layer, there is no need to provide the electron-transporting layer. Further, other layers may be provided as necessary. Examples of the other layers include, but are not limited to, an electron-blocking layer and a hole-blocking layer.

In addition, the organic EL device of the present invention has the hole-injecting layer and one or more layers of the light-emitting layer as essential layers. The light-emitting layer may be a single light-emitting layer or a light-emitting layer having a multi-layer structure obtained by laminating a plurality of light-emitting layers.

FIG. 2 illustrates another aspect of the organic EL device of the present invention. FIG. 2 illustrates an example of a device configuration obtained by tandemly laminating the basic device configurations in FIG. 1. The anode 2, the hole-injecting layer 3, the hole-transporting layer 4, the light-emitting layer 5, the electron-transporting layer 6, the electron-injecting layer 7, and the cathode 8 are laminated on the substrate 1. Of those, a plurality of units having the hole-injecting layer 3 to the electron-injecting layer 7 laminated are laminated between both terminals. The number of the units to be laminated may be modified as appropriate. Further, a metal thin film may be sandwiched between the electron-injecting layer and the hole-injecting layer adjacent to each other. The details of the respective layers are the same as those in the basic configuration in FIG. 1.

Preferred configuration examples of the organic EL device of the present invention are described below. However, the present invention is not limited thereto.

A. Single Layer Configuration Examples

1) Anode/hole-injecting layer/hole-transporting layer/light-emitting layer/electron-transporting layer/electron-injecting layer/cathode
2) Anode/hole-injecting layer/hole-transporting layer/light-emitting layer/light-emitting layer/electron-transporting layer/electron-injecting layer/cathode
3) Anode/hole-injecting layer/light-emitting layer/electron-transporting layer/electron-injecting layer/cathode B. Multi-Layer Configuration Examples 1) Anode/hole-injecting layer/hole-transporting layer/light-emitting layer/electron-transporting layer/electron-injecting layer/hole-injecting layer/hole-transporting layer/light-emitting layer/electron-transporting layer/electron-injecting layer/cathode
2) Anode/hole-injecting layer/hole-transporting layer/light-emitting layer/electron-transporting layer/electron-injecting layer/metal thin film/hole-injecting layer/hole-transporting layer/light-emitting layer/electron-transporting layer/electron-injecting layer/cathode
3) Anode/hole-injecting layer/hole-transporting layer/light-emitting layer/light-emitting layer/electron-transporting layer/electron-injecting layer/metal thin film/hole-injecting layer/hole-transporting layer/light-emitting layer/light-emitting layer/electron-transporting layer/electron-injecting layer/cathode As described above, the device configuration of the present invention may be a single layer structure having a single layer of the basic device configuration as illustrated in FIG. 1, or may be a multi-layer structure having multiple layers of the configuration. The multi-layer structure has a plurality of hole-injecting layers, and at least one or preferably all of the hole-injecting layers are hole-injecting layers each containing the compound of the general formula (1). The performance of the device is improved both in the single layer structure and in the multi-layer structure by providing such hole-injecting layers. The effect is large upon application to the multi-layer structure.

Hereinafter, the respective layers are described in detail.

(1) Substrate

The substrate 1 serves as a support member of the organic electroluminescent device. For example, a quartz or glass plate, a metal plate or a metal foil, or a plastic film or sheet is used for the substrate. In particular, a glass plate or a plate formed of a transparent synthetic resin such as polyester, polymethacrylate, polycarbonate, or polysulfone is preferred. In the case of using a synthetic resin substrate, gas barrier property must be noted. Too small gas barrier property of the substrate is not preferred because the air that has passed through the substrate may deteriorate the organic electroluminescent device. Therefore, a method involving providing a fine silicon dioxide film or the like on at least one surface of the synthetic resin substrate to ensure gas barrier property is also one of preferred methods.

(2) Anode

The anode 2 is provided on the substrate 1. In general, the anode is formed of a metal such as aluminum, gold, silver, nickel, palladium, or platinum, a metal oxide such as an oxide of indium and/or tin, an oxide of zinc and/or tin, or an oxide of tungsten and/or tin, a metal halide such as copper iodide, carbon black, or a conductive polymer such as poly(3-methylthiophene), polypyrrole, or polyaniline, for example. In general, the anode is often formed by a sputtering method, a vacuum deposition method, or the like. Further, in the case of using fine particles of a metal such as silver, fine particles of copper iodide and the like, carbon black, fine particles of a conductive metal oxide, fine powders of a conductive polymer, and the like, those may also be dispersed in an appropriate binder resin solution and applied onto a substrate to form an anode. In addition, in the case of using a conductive polymer, an anode may also be formed by forming a thin film directly on a substrate by electrolytic polymerization or by applying the conductive polymer onto a substrate. It is also possible to form the anode by laminating a different substance. The thickness of the anode 2 varies depending on required transparency. When the transparency is required, the visible light transmittance is preferably set to generally 60% or more or preferably 80% or more. The anode 2 has a thickness of generally 1 to 1000 nm or preferably 10 to 500 nm. It should be noted that, when the transparency is not required, the anode may be identical with the substrate. Further, it is also possible to further laminate a different conductive material on the above-mentioned anode.

(3) Hole-Injecting Layer

The hole-injecting layer 3 is provided on the anode 2. Used for the hole-injecting layer is a material including at least one kind of compound selected from compounds represented by the above-mentioned general formula (1). The hole-injecting layer may be formed of each of the compounds of the general formula (1) alone or a mixture of the compounds, or may be formed of a mixture with another hole-injecting material. Further, as described above, the hole-injecting layer 3 may contain a hole-transporting material. The blending amount of the compounds represented by the general formula (1) is as described above. When the compounds are each used in combination with an n-type material and used as a dopant, a given effect is exerted even in an amount of 0.1 wt % or more. On the other hand, when the compounds are mixed with another hole-injecting material before use, it is preferred to use the compounds in an amount of 50 wt % or more in order to exhibit the effects of the present invention sufficiently.

Examples of the another hole-injecting material include a phthalocyanine compound such as copper phthalocyanine, an organic compound such as polyaniline or polythiophene, and a metal oxide such as vanadium oxide, ruthenium oxide, or molybdenum oxide.

The hole-injecting layer may be formed by forming the above-mentioned hole-injecting material into a thin film by a known method such as a vacuum deposition method, a spin coat method, a cast method, a printing method including an ink-jet method, or an LB method.

The hole-injecting layer has a thickness of 30 nm or less, preferably 20 nm or less, or more preferably 5 to 15 nm when the layer is formed of the compound of the general formula (1) alone. A thickness equal to or more than the above-mentioned value deteriorates a hole-injecting characteristic, which causes an increase in driving voltage, a decrease in efficiency, and besides, a decrease in driving stability of the organic EL device. Further, the hole-injecting layer has a thickness of generally 1 to 300 nm or preferably 5 to 100 nm when the layer is formed of a mixed layer of the compound of the general formula (1) and another hole-injecting material.

Further, the hole-transporting material may also be incorporated into the hole-injecting layer. Also in this case, the hole-injecting layer has a thickness of generally 1 to 300 nm or preferably 5 to 100 nm. When the hole-transporting material is incorporated into the hole-injecting layer, there is no need to provide the hole-transporting layer adjacent to the hole-injecting layer.

(4) Hole-Transporting Layer

The hole-transporting layer 4 is provided on the hole-injecting layer 3. The hole-transporting layer plays a role in efficiently transporting holes from the anode to the light-emitting layer. The hole-transporting material contained in the hole-transporting layer is not particularly limited as long as the material is a compound having hole-transporting property, and is preferably a compound having an IP of 6.0 eV or less or more preferably 5.8 eV or less. An IP more than the above-mentioned value prevents holes from being smoothly transferred from the hole-injecting layer to the hole-transporting layer, which causes an increase in driving voltage, a decrease in efficiency, and besides, a decrease in driving stability of the organic EL device.

Examples of the hole-transporting material include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive polymeric oligomer, in particular, a thiophene oligomer.

To be specific, it is preferred to use such an arylamine-based hole-transporting material as described below.

Representative examples of the arylamine-based hole-transporting material include N,N,N',N'-tetraphenyl-4,4'-diaminophenyl; N,N'-diphenyl-N,N'-bis(3-methylphenyl)-[1,1'-biphenyl]-4,4'-di amine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino)quadriphenyl; N,N,N-tri(p-tolyl)amine; 4-(di-p-tolylamino)-4'-[4-(di-p-tolylamino) styryl]stilbene; 4-N,N-diphenylamino-(2-diphenylvinyl)benzene; 3-methoxy-4'-N,N-diphenylaminostilbenzene; N-phenylcarbazole; 4,4-bis[N-(1-naphthyl)-N-phenylamino]biphenyl (α-NPD) having two fused aromatic rings in the molecule, and 4,4',4"-tris[N-(3-methylphenyl)-N-phenylamino]triphenylamine (MT-DATA) having three triphenylamine units linked in a starburst fashion.

The hole-transporting layer has a thickness of generally 1 to 300 nm or preferably 5 to 100 nm, and is formed as a thin film on the hole-injecting layer by the same method as in the hole-injecting layer. The hole-transporting layer may have a single layer structure formed of one kind or two or more kinds of materials described above.

(5) Light-Emitting Layer

The light-emitting layer 5 is provided on the hole-transporting layer 4. The light-emitting layer has a function of allowing holes and electrons to recombine with each other to emit light.

The light-emitting layer may be formed of a single light-emitting layer, or may be formed by laminating a plurality of light-emitting layers adjacent to each other. It should be noted that the light-emitting layer is formed of a host material and a fluorescent light-emitting material or a phosphorescent light-emitting material, and any suitable material which has hitherto been used for the formation of such layer may be used. Further, when the light-emitting layer contains the hole-transporting material, there is no need to provide the hole-transporting layer between the hole-injecting layer and the light-emitting layer.

Examples of the host material include a fused ring derivative such as anthracene or pyrene, which has been known as a light emitter heretofore, a metal chelated oxinoid compound such as tris(8-quinolinolato)aluminum, a bisstyryl derivative such as a bisstyrylanthracene derivative or a distyrylbenzene derivative, a tetraphenylbutadiene derivative, a coumarin derivative, an oxadiazole derivative, a pyrrolopyridine derivative, a perinone derivative, a cyclopentadiene derivative, an oxadiazole derivative, a thiadiazolopyridine derivative, and a polymer-based derivative such as a polyphenylene vinylene derivative, a polyparaphenylene derivative, and a polythiophene derivative.

Examples of the fluorescent light-emitting material to be added to the host material include a fused ring derivative such as perylene or rubrene, a quinacridone derivative, Phenoxazone 660, DCM1, perinone, a coumarin derivative, a pyrromethene (diazaindacene) derivative, and a cyanine pigment.

The phosphorescent light-emitting material to be added to the host material preferably contains an organic metal complex including at least one metal selected from ruthenium, rhodium, palladium, silver, rhenium, osmium, iridium, platinum, gold, and the like.

Preferred examples of the phosphorescent light-emitting material serving as a dopant include complexes such as Ir(ppy)3, complexes such as Ir(bt)2.acac3, and complexes such as PtOEt3, the complexes each having a noble metal element such as Ir as a central metal.

The light-emitting layer has a thickness of generally 1 to 300 nm or preferably 5 to 100 nm, and is formed as a thin film on the hole-transporting layer by the same method as in the hole-injecting layer. It is also preferred to successively laminate a plurality of light-emitting layer materials to form a light-emitting layer having a multi-layer structure. Also in this case, the thickness of the light-emitting layer preferably falls within the above-mentioned range.

(6) Electron-Transporting Layer

The electron-transporting layer 6 is provided on the light-emitting layer 5. When the light-emitting layer contains an electron-transporting material, there is no need to provide the electron-transporting layer. The electron-transporting layer is formed of a compound capable of efficiently transporting electrons injected from a cathode in the direction of the light-emitting layer between electrodes applied with an electric field. An electron-transporting compound used for the electron-transporting layer must be a compound that is high in electron-transporting efficiency from a cathode, has a high electron mobility, and can transport injected electrons efficiently.

Examples of the electron-transporting material satisfying such conditions include a metal complex such as Alq3, a metal complex of 10-hydroxybenzo[h]quinoline, an oxadiazole derivative, a distyrylbiphenyl derivative, a silole derivative, a 3- or 5-hydroxyflavone metal complex, a benzoxazole metal complex, a benzothiazole metal complex, tris(benzimidazolyl)benzene, a quinoxaline compound, a phenanthroline derivative, 2-t-butyl-9,10-N,N'-dicyanoanthraquinonediimine, n-type hydrogenated amorphous silicon carbide, n-type zinc sulfide, and n-type zinc selenide.

The electron-transporting layer has a thickness of generally 1 to 300 nm or preferably 5 to 100 nm, and is formed as a thin film on the light-emitting layer by the same method as in the hole-injecting layer. The electron-transporting layer may have a single layer structure formed of one kind or two or more kinds of materials described above.

(7) Electron-Injecting Layer

In addition, the formation of the electron-injecting layer 7 on the electron-transporting layer 6 is also an effective method of improving the efficiency of the device. The electron-injecting layer plays a role in injecting electrons into the light-emitting layer.

Specific examples of the electron-injecting material include: an alkali metal salt, an alkaline earth metal salt, an alkali metal oxide, or an alkaline earth metal salt such as LiF, $MgF_2$, or $Li_2O$; an alkali metal complex such as Liq; and an alkali metal or an alkaline earth metal such as Li, Cs, or Ca.

The electron-injecting layer has a thickness of generally 0.1 to 300 nm or preferably 0.5 to 50 nm, and is formed as a thin film on the light-emitting layer or the electron-transporting layer by the same method as in the hole-injecting layer.

The electron-injecting layer may be a layer formed of the above-mentioned material alone or a layer formed of a mixture of the electron-injecting material and the electron-transporting layer material at any suitable ratio. In this case, any one of the electron-injecting layer or the electron-transporting layer may be omitted.

(8) Cathode

The cathode 8 plays a role in injecting electrons into the electron-injecting layer. A material used for the cathode may be the material used for the anode. However, it is preferred to use a low work function metal in order to inject electrons efficiently, and an appropriate metal such as tin, magnesium, indium, calcium, aluminum, lithium, or silver, or an alloy thereof is used. To be specific, there is exemplified an electrode formed of a low work function alloy such as a magnesium-silver alloy, a magnesium-indium alloy, or an aluminum-lithium alloy.

Further, the stability of the device is increased by further laminating a layer formed of a metal having a high work function and being stable in the air on a cathode formed of a low work function metal for the purpose of protecting the cathode. For that purpose, a metal such as aluminum, silver, copper, nickel, chromium, gold, or platinum is used.

The cathode has a thickness of generally 1 to 1000 nm or preferably 10 to 500 nm, and is formed as a thin film on the electron-injecting layer or a light emission unit by the same method as in the hole-injecting layer. The cathode may have a single layer structure formed of one kind or two or more kinds of materials described above.

Further, a transparent or translucent cathode may be prepared by preparing a film being formed of the above-mentioned metal and having a thickness of 1 nm to 20 nm on a cathode and then preparing a film formed of the conductive transparent material exemplified in the description about the anode on the film. The application of the method also allows for the production of a device in which both the anode and the cathode have transparency.

Also in the case of the organic EL device having such a multi-layer structure as illustrated in FIG. 2, the respective layers may be formed in accordance with the above-mentioned description. For example, the hole-injecting layer 3 to the electron-injecting layer 7 are successively provided on the anode 2 to prepare a first unit (I). Next, the hole-injecting layer 3 to the electron-injecting layer 7 are successively provided on the electron-injecting layer 7 serving as the uppermost layer of the unit (I) to prepare a second unit (II). In addition, in the same manner, a third unit (III) to an N-th unit (N) may be provided similarly. The cathode 8 is provided on the electron-injecting layer 7 of the unit (N). It should be noted that each of the above-mentioned units is mainly formed of the light-emitting layer, and hence is also referred to as a light emission unit. Further, parts represented by reference numerals in FIG. 2 are identical with those in FIG. 1.

It should be noted that a structure opposite to that in FIG. 1, that is, a structure in which the cathode 8, the electron-injecting layer 7, the electron-transporting layer 6, the light-emitting layer 5, the hole-transporting layer 4, the hole-injecting layer 3, and the anode 2 are laminated on the substrate 1 in the stated order may be adopted, and the organic EL device of the present invention may also be provided between two substrates, at least one of which has high transparency, as described above. Also in this case, it is possible to add or omit layers as necessary. The same holds true for the case of the multi-layer structure as illustrated in FIG. 2.

Further, the present invention is applicable to any one of the case where the organic EL device is a single device, the case where the devices of this kind are arranged in an array fashion, and the case where the device has a structure in which an anode and a cathode are arranged in an X-Y matrix fashion. According to the organic EL device of the present invention, the use of the compound of the general formula (1) in the hole-injecting layer provides a device exhibiting high luminous efficiency at a lower voltage than ever before and having greatly improved driving stability, which can exhibit excellent performance in the applications to full-color or multi-color panels. In addition, the use of a triarylamine-based compound in the hole-transporting layer increases the effect.

EXAMPLES

Hereinafter, the present invention is described by way of examples. However, the present invention is not limited thereto.

Figure 3:
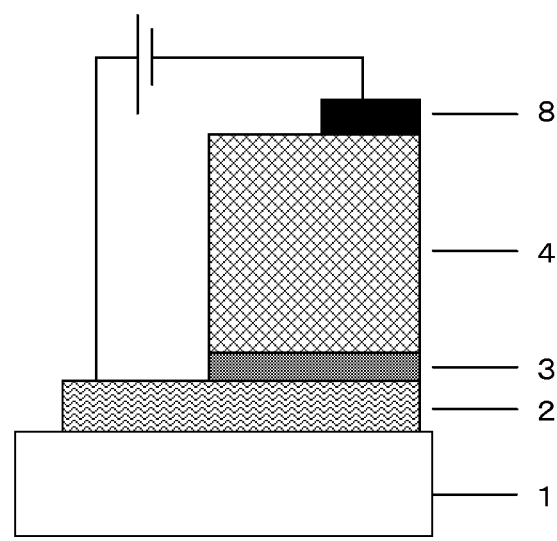
FIG. 3 is a schematic cross-sectional view illustrating a device for evaluation of hole-injecting/transporting property.

A test for evaluating hole-injecting/transporting property was performed using such a device for evaluation as illustrated in FIG. 3. The device for evaluation has the anode 2, the hole-injecting layer 3, the hole-transporting layer 4, and the cathode 8 on the glass substrate 1.

Example 1

In FIG. 3, on a glass substrate, on which an anode electrode being formed of ITO and having a thickness of 150 nm had been formed, the respective thin films were laminated at a degree of vacuum of $1.0 \times 10^{-5}$ Pa by a vacuum deposition method. First, Exemplified Compound 1 was used as a material for forming a hole-injecting layer to form a hole-injecting layer having a thickness of 10 nm on ITO. Next, 4,4'-bis(N-(1-naphthyl)-N-phenylamino)biphenyl (NPB) was used to form a hole-transporting layer having a thickness of 110 nm. Finally, aluminum (Al) was used to form a cathode electrode having a thickness of 100 nm on the hole-transporting layer. Thus, a device for evaluation of hole-injecting/transporting property was prepared.

Example 2

A device for evaluation was prepared in the same manner as in Example 1 except that Exemplified Compound 14 was used as the material for a hole-injecting layer.

Comparative Example 1

A device for evaluation was prepared in the same manner as in Example 1 except that copper-phthalocyanine (CuPc) was used as the material for forming a hole-injecting layer.

Comparative Example 2

A device for evaluation was prepared in the same manner as in Example 1 except that 1,4,5,8-naphthalenetetracarboxylic acid dianhydride (NTCDA) was used as the material for forming a hole-injecting layer.

The resultant device for evaluation of hole-injecting/transporting property was connected to an exterior power source and applied with a DC voltage. The results confirmed that the device had such a current-voltage characteristic as shown in Table 1. The current density in Table 1 represents a current density value ($A/m^2$) at 5 V. As shown in Table 1, it is understood that the hole-injecting material of the present invention exhibits more satisfactory hole-injecting property even at the same voltage. It should be noted that NPB has an IP of 5.4 eV.

TABLE 1

| | Hole-injecting material Thickness (10 nm) | Hole-transporting layer material | Current density at 5 V ($A/m^2$) |
|---|---|---|---|
| Example 1 | Compound 1 | NPB | 10,000 |
| Example 2 | Compound 14 | NPB | 500 |
| Comparative Example 1 | CuPc | NPB | 200 |
| Comparative Example 2 | NTCDA | NPB | 350 |

Example 3

A device for evaluation was prepared in the same manner as in Example 1 except that the hole-injecting layer had a thickness of 20 nm and the hole-transporting layer had a thickness of 100 nm.

Comparative Example 3

A device for evaluation was prepared in the same manner as in Example 3 except that NTCDA was used as the material for forming a hole-injecting layer.

The resultant device for evaluation of hole-injecting/transporting property was connected to an exterior power source and applied with a DC voltage. The results confirmed that the device had such a current-voltage characteristic as shown in Table 2.

TABLE 2

| | Hole-injecting material Thickness (20 nm) | Hole-transporting layer material | Current density at 5 V ($A/m^2$) |
|---|---|---|---|
| Example 3 | Compound 1 | NPB | 500 |
| Comparative Example 3 | NTCDA | NPB | 200 |

Example 4

In FIG. 1, on a glass substrate, on which an anode electrode being formed of ITO and having a thickness of 110 nm had been formed, the respective thin films were laminated at a degree of vacuum of $1.0 \times 10^{-5}$ Pa by a vacuum deposition method. First, Exemplified Compound 1 was used to form a hole-injecting layer having a thickness of 10 nm on ITO. Next, NPB was used to form a hole-transporting layer having a thickness of 25 nm. Next, 9,10-di(2-naphthyl)anthracene (DNA) and 2,5,8,11-tetra-tert-butylperylene (TBP) were co-deposited from the vapor from different deposition sources so that the amount of TBP may be 1.0% by weight, to thereby form a light-emitting layer having a thickness of 30 nm on the hole-transporting layer. Next, tris(8-quinolinolato)aluminum complex (Alq3) was used to form an electron-transporting layer having a thickness of 30 nm. In addition, Alq3 and (8-quinolinolato) lithium complex (Liq) were co-deposited from the vapor from different deposition sources so that the amount of Liq may be 25% by weight, to thereby form an electron-injecting layer having a thickness of 10 nm on the electron-transporting layer. Finally, aluminum (Al) was used to form a cathode electrode having a thickness of 100 nm on the electron-injecting layer. Thus, a one-unit organic EL device was prepared.

Example 5

An organic EL device was prepared in the same manner as in Example 4 except that a mixed layer of Exemplified Compound 1 and NPB (at a weight ratio of 50:50) having a thickness of 10 nm was used as the hole-injecting layer.

Comparative Example 4

An organic EL device was prepared in the same manner as in Example 4 except that an NTCDA layer was used as the hole-injecting layer.

The resultant organic EL device was connected to an exterior power source and applied with a DC voltage. The results confirmed that the device had such a light emission characteristic as shown in Table 3. In Tables 3 to 6, values for luminance, voltage, and luminous efficiency are values at 100 $A/m^2$, and values for LT50 are values at 250 $A/m^2$.

TABLE 3

| | Driving voltage (V) | Current efficiency (cd/A) | LT50 (h) |
|---|---|---|---|
| Example 4 | 4.1 | 6.5 | 1300 |
| Example 5 | 4.0 | 6.2 | 1200 |
| Comparative Example 4 | 5.2 | 6.0 | 700 |

Example 6

In FIG. 1, on a glass substrate, on which an anode electrode being formed of ITO and having a thickness of 110 nm had been formed, the respective thin films were laminated at a degree of vacuum of $1.0 \times 10^{-5}$ Pa by a vacuum deposition method. First, Exemplified Compound 1 was used to form a hole-injecting layer having a thickness of 10 nm on ITO. Next, NPB was used to form a hole-transporting layer having a thickness of 10 nm. Next, NPB and rubrene (5,6,11,12-tetraphenyltetracene) were co-deposited from the vapor from different deposition sources so that the amount of rubrene may be 1.0% by weight, to thereby form a first light-emitting layer having a thickness of 20 nm on the hole-transporting layer. Next, 9,10-di(2-naphthyl)anthracene (DNA) and 2,5,8,11-tetra-tert-butylperylene (TBP) were co-deposited from the vapor from different deposition sources so that the amount of TBP may be 1.0% by weight, to thereby form a second light-emitting layer having a thickness of 30 nm. Next, tris (8-quinolinolato)aluminum complex (Alq3) was used to form an electron-transporting layer having a thickness of 30 nm. In addition, Alq3 and (8-quinolinolato) lithium complex (Liq) were co-deposited from the vapor from different deposition sources so that the amount of Liq may be 25% by weight, to thereby form an electron-injecting layer having a thickness of 10 nm on the electron-transporting layer. Finally, aluminum (Al) was used to form a cathode electrode having a thickness of 100 nm on the electron-injecting layer. Thus, a one-unit organic EL device was prepared.

Example 7

An organic EL device was prepared in the same manner as in Example 6 except that the hole-transporting layer was omitted and the first light-emitting layer had a thickness of 30 nm.

Comparative Example 5

An organic EL device was prepared in the same manner as in Example 6 except that NTCDA was used as the hole-injecting layer material.

The resultant organic EL device was connected to an exterior power source and applied with a DC voltage. The results confirmed that the device had such a light emission characteristic as shown in Table 4.

TABLE 4

| | Driving voltage (V) | Current efficiency (cd/A) | LT50 (h) |
|---|---|---|---|
| Example 6 | 5.5 | 13.5 | 2000 |
| Example 7 | 5.2 | 12.2 | 1800 |
| Comparative Example 5 | 6.5 | 11.0 | 1000 |

Example 8

In FIG. 2, on a glass substrate, on which an anode electrode being formed of ITO and having a thickness of 110 nm had been formed, the respective thin films were laminated at a degree of vacuum of $1.0 \times 10^{-5}$ Pa by a vacuum deposition method. First, Exemplified Compound 1 was used to form a hole-injecting layer having a thickness of 10 nm on ITO. Next, NPB was used to form a hole-transporting layer having a thickness of 25 nm. Next, NPB and rubrene were co-deposited from the vapor from different deposition sources so that the amount of rubrene may be 1.0% by weight, to thereby form a first light-emitting layer having a thickness of 20 nm on the hole-transporting layer. Next, DNA and TBP were co-deposited from the vapor from different deposition sources so that the amount of TBP may be 1.0% by weight, to thereby form a second light-emitting layer having a thickness of 30 nm. Next, Alq3 was used to form an electron-transporting layer having a thickness of 30 nm. In addition, Alq3 and Liq were co-deposited from the vapor from different deposition sources in an amount of Liq of 25% by weight so as to have a thickness of 10 nm, and Al was then deposited from the vapor at a rate of 0.05 nm/s so as to have a thickness of 2 nm, to thereby form an electron-injecting layer on the electron-transporting layer. Next, Exemplified Compound 1 was deposited again at the same rate as described above to form a hole-injecting layer having a thickness of 50 nm. Subsequently, the respective films of from a hole-transporting layer to an electron-injecting layer were formed as described above. Finally, aluminum (Al) was used to form a cathode electrode having a thickness of 100 nm on the electron-injecting layer. Thus, a two-unit organic EL device was prepared.

Comparative Example 6

A two-unit organic EL device was prepared in the same manner as in Example 8 except that NTCDA was used as the hole-injecting layer material.

The resultant organic EL device was connected to an exterior power source and applied with a DC voltage. The results confirmed that the device had such a light emission characteristic as shown in Table 5.

TABLE 5

| | Driving voltage (V) | Current efficiency (cd/A) | LT50 (h) |
|---|---|---|---|
| Example 8 | 11.0 | 13.5 | 3000 |
| Comparative Example 6 | 15.0 | 11.0 | 1000 |

INDUSTRIAL APPLICABILITY

According to the organic EL device of the present invention, there can be provided a device exhibiting high luminous efficiency even at a low voltage and having greatly improved driving stability as compared to a conventional technology. In addition, there can be provided a device that is hardly deteriorated during being stored at high temperatures. As a result, the device can exhibit excellent performance in applications to full-color or multi-color panels. Therefore, potential applications of the organic electroluminescent device according to the present invention include a flat panel display (such as a display for an OA computer or a wall-hung TV), an on-vehicle display device, a cellular phone display, a light source utilizing the feature of the device as a planar light emitter (such as a light source for a copying machine or a backlight source for liquid crystal displays and meters), a display board, and a marker lamp. Accordingly, the device has a large technical value.

The invention claimed is:
1. An organic electroluminescent device, comprising at least one light-emitting layer and at least one hole-injecting layer between an anode and a cathode arranged opposite to each other, wherein the organic electroluminescent device comprises a hole-injecting layer containing a carboxylic acid derivative represented by the following general formula (1):

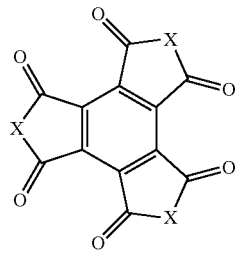
(1)

where: X represents O or N—R; and R represents H or a monovalent substituent.

2. The organic electroluminescent device according to claim 1, comprising a hole-transporting material having an ionization potential of 6.0 eV or less in at least one layer of the hole-injecting layer containing the carboxylic acid derivative represented by the general formula (1) and a layer adjacent to the hole-injecting layer.

3. The organic electroluminescent device according to claim 2, wherein the layer adjacent to the hole-injecting layer is a hole-transporting layer or a light-emitting layer.

4. The organic electroluminescent device according to claim 2, wherein the hole-transporting material having an ionization potential of 6.0 eV or less comprises an arylamine-based hole-transporting material.

* * * * *